United States Patent [19]

Peery et al.

[11] Patent Number: 5,516,655
[45] Date of Patent: May 14, 1996

[54] **MULTIPLE DRUG RESISTANCE GENE OF *AUREOBASIDIUM PULLULANS***

[75] Inventors: Robert B. Peery, Indianapolis; Paul L. Skatrud, Greenwood, both of Ind.

[73] Assignee: Eli Lilly and Company, Indianapolis, Ind.

[21] Appl. No.: 232,537

[22] Filed: Apr. 20, 1994

[51] Int. Cl.[6] ............ C12N 1/19; C12N 15/11; C12N 15/31; C12N 15/81
[52] U.S. Cl. .......... 435/69.1; 435/252.3; 435/254.11; 435/320.1; 536/23.74
[58] Field of Search .................. 435/69.1, 172.3, 435/320.1, 252.3, 254.11, 911, 240.2, 240.4; 536/23.74; 530/823, 350

[56] References Cited

U.S. PATENT DOCUMENTS 5,057,493  10/1991  Takesako et al. .................. 514/11
5,158,876  10/1992  Takesako et al. .................. 435/71.1

FOREIGN PATENT DOCUMENTS

92/11034  7/1992  WIPO .

OTHER PUBLICATIONS

Tiligada, E. et al., 1993, Br. J. Pharmacol. 108:233.
Gottesman, M. et al., Feb. 1983, TIPS 91:54–58.
Fojo, A. et al., 1987, Proc. Natl. Acad. Sci. USA 84:265–269.
Gottesman, M. et al., 1993, Annu. Rev. Biochem. 62:385–427.
Pastan, I. et al., 1991, Annu. Rev. Med. 42:277–286.
Gottesman, M. et al., 1988, J. of Biol. Chem. 263(25):12163–12166.
Raymond, M. et al., 1994, Mol. and Cell. Biol. 14(1):277–286.
Ruetz, S. et al., 1993, Proc. Natl. Acad. Sci. USA 90:11588–11592.
Raymond, M. et al., 1992, Science 256:232–234.
Pastan, I. et al. 1987, New Eng. J. of Med. 316(22):1388–1393.
Maniatis, T. et al. *Molecular Cloning: A Laboratory Manual*, 2nd Edition (1989), pp. 1.74–1.84.

*Primary Examiner*—Dian C. Jacobson
*Attorney, Agent, or Firm*—Thomas G. Plant

[57] ABSTRACT

The invention provides isolated nucleic acid compounds encoding the multiple drug resistance protein of *Aureobasidium pullulans*. Vectors and transformed host cells comprising the multiple drug resistance-encoding DNA of *Aureobasidium pullulans* are also provided. The invention further provides assays which utilize these transformed host cells.

15 Claims, 1 Drawing Sheet

FIGURE 1

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 3909 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

```
ATG  TCT  TCT  GCC  GAC  GGC  AGA  CGA  ACA  GTT  TCA  TCT  GAT  TAT  GGC  CAT        48
Met  Ser  Ser  Ala  Asp  Gly  Arg  Arg  Thr  Val  Ser  Ser  Asp  Tyr  Gly  His
  1              5                        10                       15

CCA  CGA  CCT  TCA  ATG  GCC  AAC  GTC  GAA  GCG  GAT  CAC  AAC  TTT  GAG  ACG        96
Pro  Arg  Pro  Ser  Met  Ala  Asn  Val  Glu  Ala  Asp  His  Asn  Phe  Glu  Thr
                  20                       25                       30

ACG  ACT  TTG  AAT  TCT  GCT  CAA  CCG  CGA  TCA  TGG  CAC  ACT  GAG  TTT  GTC       144
Thr  Thr  Leu  Asn  Ser  Ala  Gln  Pro  Arg  Ser  Trp  His  Thr  Glu  Phe  Val
             35                       40                       45

TTC  GTC  TCC  CGG  AAA  TTG  ATT  CAA  CAA  ATT  CTT  GGT  AAA  AAT  CCG  TTC       192
Phe  Val  Ser  Arg  Lys  Leu  Ile  Gln  Gln  Ile  Leu  Gly  Lys  Asn  Pro  Phe
```

| | | | | | | | | | | | | | | | | |
|---|---|---|---|---|---|---|---|---|---|---|---|---|---|---|---|---|
| AAG | AGT | TCA | TAT | CTG | GAT | TTG | TTC | AAG | CTT | GTC | AAC | GAT | GCG | AAG | TCG | 240 |
| Lys | Ser | Ser | Tyr | Leu | Asp | Leu | Phe | Lys | Leu | Val | Asn | Asp | Ala | Lys | Ser | |
| 65 | | | | 70 | | | | | 75 | | | | | | 80 | |
| AAG | GCC | GTT | CTT | TGG | GCT | GGC | ATA | CTG | TTG | GCA | ATA | GCT | GCT | GGT | TGT | 288 |
| Lys | Ala | Val | Leu | Trp | Ala | Gly | Ile | Leu | Leu | Ala | Ile | Ala | Ala | Gly | Cys | |
| | | | | 85 | | | | | 90 | | | | | 95 | | |
| CCA | TTG | CCC | ATC | ATT | GGC | TAT | ATT | TTC | GGC | CAG | ATC | ATT | ACT | TCT | TTC | 336 |
| Pro | Leu | Pro | Ile | Ile | Gly | Tyr | Ile | Phe | Gly | Gln | Ile | Ile | Thr | Ser | Phe | |
| | | | 100 | | | | | 105 | | | | | 110 | | | |
| CCG | CCT | CCG | GAA | GAT | GTT | CTG | CGA | GAT | AGA | CTG | TAT | CAG | CTT | GTT | GGT | 384 |
| Pro | Pro | Pro | Glu | Asp | Val | Leu | Arg | Asp | Arg | Leu | Tyr | Gln | Leu | Val | Gly | |
| | | 115 | | | | | 120 | | | | | 125 | | | | |
| GTC | GCT | TGT | GGC | TAC | TTT | ATC | GTT | ACG | ACT | GGA | TAT | GCA | ATT | GCG | TGG | 432 |
| Val | Ala | Cys | Gly | Tyr | Phe | Ile | Val | Thr | Thr | Gly | Tyr | Ala | Ile | Ala | Trp | |
| 130 | | | | | 135 | | | | | 140 | | | | | | |
| GGA | TTG | ACT | GGA | GAG | AAG | ATC | TCG | CGT | CGT | TTT | CGA | GAA | ACG | CTT | GTT | 480 |
| Gly | Leu | Thr | Gly | Glu | Lys | Ile | Ser | Arg | Arg | Phe | Arg | Glu | Thr | Leu | Val | |
| 145 | | | | | 150 | | | | | 155 | | | | | 160 | |
| GAG | CGC | CTG | CTT | GGT | CTT | GAG | CAG | GCA | TAC | TTC | GAC | ATC | AAA | GAT | CCA | 528 |
| Glu | Arg | Leu | Leu | Gly | Leu | Glu | Gln | Ala | Tyr | Phe | Asp | Ile | Lys | Asp | Pro | |
| | | | | 165 | | | | | 170 | | | | | 175 | | |
| GAC | ATT | ACG | AAC | CTT | CTG | ACC | GAG | AAG | ATT | GAA | GCG | ATC | CAG | ATA | GGA | 576 |
| Asp | Ile | Thr | Asn | Leu | Leu | Thr | Glu | Lys | Ile | Glu | Ala | Ile | Gln | Ile | Gly | |
| | | | 180 | | | | | 185 | | | | | 190 | | | |
| ACA | TCT | GAA | AAA | GTC | GGC | ATA | TTC | ATC | CAG | TCG | ATC | AGC | TAC | TTC | GTT | 624 |
| Thr | Ser | Glu | Lys | Val | Gly | Ile | Phe | Ile | Gln | Ser | Ile | Ser | Tyr | Phe | Val | |
| | | | 195 | | | | | 200 | | | | | 205 | | | |
| GCT | GCC | TTT | ATT | GTT | GGG | TTC | ATC | TTG | AAC | GCC | AAA | CTC | ACC | GGT | ATT | 672 |
| Ala | Ala | Phe | Ile | Val | Gly | Phe | Ile | Leu | Asn | Ala | Lys | Leu | Thr | Gly | Ile | |
| | 210 | | | | | 215 | | | | | 220 | | | | | |
| CTA | TTC | GCT | GCC | GTC | ATA | CCT | CTC | ATG | GCT | TTG | ATC | GTT | ACT | GTC | GGC | 720 |
| Leu | Phe | Ala | Ala | Val | Ile | Pro | Leu | Met | Ala | Leu | Ile | Val | Thr | Val | Gly | |
| 225 | | | | | 230 | | | | | 235 | | | | | 240 | |
| TCC | TCC | AGA | ATC | GCA | AAG | TAC | ACC | AAA | GCA | GCC | ACC | GAA | TAC | ACC | GAA | 768 |
| Ser | Ser | Arg | Ile | Ala | Lys | Tyr | Thr | Lys | Ala | Ala | Thr | Glu | Tyr | Thr | Glu | |
| | | | | 245 | | | | | 250 | | | | | 255 | | |
| GCC | GCT | GGA | AGG | ATC | GCT | GAA | AGT | GCT | ATC | CAT | GCT | GTC | AAG | GTT | GTG | 816 |
| Ala | Ala | Gly | Arg | Ile | Ala | Glu | Ser | Ala | Ile | His | Ala | Val | Lys | Val | Val | |
| | | | 260 | | | | | 265 | | | | | 270 | | | |
| CAG | GCT | TTT | GGC | ATG | GCC | GAA | AAT | CTC | AGC | AAA | GAA | CAC | TAC | CGT | CTG | 864 |
| Gln | Ala | Phe | Gly | Met | Ala | Glu | Asn | Leu | Ser | Lys | Glu | His | Tyr | Arg | Leu | |
| | | 275 | | | | | 280 | | | | | 285 | | | | |
| CTC | AAA | CTG | TCT | GCA | AGA | TAC | GCC | ATC | CGG | AAG | TCA | GTT | TCT | GCT | GCG | 912 |
| Leu | Lys | Leu | Ser | Ala | Arg | Tyr | Ala | Ile | Arg | Lys | Ser | Val | Ser | Ala | Ala | |
| | 290 | | | | | 295 | | | | | 300 | | | | | |
| TTC | ATG | CTT | GGC | TTG | GTC | TAT | TTT | ACT | GCT | TAC | AGT | GCC | AAT | GCG | CTT | 960 |
| Phe | Met | Leu | Gly | Leu | Val | Tyr | Phe | Thr | Ala | Tyr | Ser | Ala | Asn | Ala | Leu | |
| 305 | | | | | 310 | | | | | 315 | | | | | 320 | |
| GCC | TTT | TGG | GAG | GGC | TCA | CGT | CTC | GCT | GCA | GAA | TCT | GGC | TCA | AAC | AAT | 1008 |
| Ala | Phe | Trp | Glu | Gly | Ser | Arg | Leu | Ala | Ala | Glu | Ser | Gly | Ser | Asn | Asn | |
| | | | | 325 | | | | | 330 | | | | | 335 | | |
| GCT | GGT | ACC | GTC | TAT | GCC | GTG | GTC | TTC | TTG | ATT | ATA | GAC | GCT | TCG | TTT | 1056 |
| Ala | Gly | Thr | Val | Tyr | Ala | Val | Val | Phe | Leu | Ile | Ile | Asp | Ala | Ser | Phe | |
| | | | 340 | | | | | 345 | | | | | 350 | | | |
| GTT | GTC | GGC | CAA | TTT | GGA | CCA | TTC | CTT | GGT | AGC | TTC | GCC | ACC | GCT | GCA | 1104 |
| Val | Val | Gly | Gln | Phe | Gly | Pro | Phe | Leu | Gly | Ser | Phe | Ala | Thr | Ala | Ala | |
| | | 355 | | | | | 360 | | | | | 365 | | | | |
| GCT | GCT | GGA | GAA | AGT | GTT | TAC | GAA | ATC | CTC | AAC | CAT | CCA | CAG | TCT | GAA | 1152 |
| Ala | Ala | Gly | Glu | Ser | Val | Tyr | Glu | Ile | Leu | Asn | His | Pro | Gln | Ser | Glu | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     | 370 |     |     |     |     | 375 |     |     |     |     | 380 |     |     |     |     |      |
| ATC | AAC | GTC | TAC | TCG | GAG | GCT | GGG | CAA | GAA | GCC | ACA | GAG | AGC | GAC | ATG | 1200 |
| Ile | Asn | Val | Tyr | Ser | Glu | Ala | Gly | Gln | Glu | Ala | Thr | Glu | Ser | Asp | Met |      |
| 385 |     |     |     |     | 390 |     |     |     |     | 395 |     |     |     |     | 400 |      |
| AAA | GCT | GAT | TTG | GTC | TTT | CGC | AAT | GTC | ACA | TTT | GTT | TAT | CCC | GCG | AGG | 1248 |
| Lys | Ala | Asp | Leu | Val | Phe | Arg | Asn | Val | Thr | Phe | Val | Tyr | Pro | Ala | Arg |      |
|     |     |     |     | 405 |     |     |     |     | 410 |     |     |     |     | 415 |     |      |
| ACA | TCT | GCT | CGT | GCT | CTG | GAA | GAG | ATG | AGT | CTT | ATC | CTC | AAA | GCC | GGA | 1296 |
| Thr | Ser | Ala | Arg | Ala | Leu | Glu | Glu | Met | Ser | Leu | Ile | Leu | Lys | Ala | Gly |      |
|     |     |     | 420 |     |     |     |     | 425 |     |     |     |     | 430 |     |     |      |
| CAG | ATG | AAC | GCG | ATT | GTC | GGC | ACG | AGT | GGT | TGC | GGC | AAA | AGC | ACT | CTT | 1344 |
| Gln | Met | Asn | Ala | Ile | Val | Gly | Thr | Ser | Gly | Cys | Gly | Lys | Ser | Thr | Leu |      |
|     |     | 435 |     |     |     |     | 440 |     |     |     |     | 445 |     |     |     |      |
| GTG | TCT | CTG | CTC | TTG | AGG | CTG | TAC | GAC | ATA | TCC | TCT | GGT | CAA | TTG | ACA | 1392 |
| Val | Ser | Leu | Leu | Leu | Arg | Leu | Tyr | Asp | Ile | Ser | Ser | Gly | Gln | Leu | Thr |      |
|     | 450 |     |     |     |     | 455 |     |     |     |     | 460 |     |     |     |     |      |
| ATA | GGA | AGC | CAT | GAT | ATC | AAG | GAC | TTC | AAC | GTA | AGG | AGT | TTG | AGA | AAA | 1440 |
| Ile | Gly | Ser | His | Asp | Ile | Lys | Asp | Phe | Asn | Val | Arg | Ser | Leu | Arg | Lys |      |
| 465 |     |     |     |     | 470 |     |     |     |     | 475 |     |     |     |     | 480 |      |
| TAC | ACA | GCC | CTG | GTA | GAC | CAA | GAC | TCT | GTC | CTG | TTC | TCT | GGT | TCG | GTC | 1488 |
| Tyr | Thr | Ala | Leu | Val | Asp | Gln | Asp | Ser | Val | Leu | Phe | Ser | Gly | Ser | Val |      |
|     |     |     |     | 485 |     |     |     |     | 490 |     |     |     |     | 495 |     |      |
| CTT | GAA | AAC | ATC | AGT | TAT | GGA | CTT | GGT | GAA | CAT | TCA | TTA | TCA | GAC | GAT | 1536 |
| Leu | Glu | Asn | Ile | Ser | Tyr | Gly | Leu | Gly | Glu | His | Ser | Leu | Ser | Asp | Asp |      |
|     |     |     | 500 |     |     |     |     | 505 |     |     |     |     | 510 |     |     |      |
| GTT | GTC | TTG | GAG | AGG | TGT | ACT | GAG | GCT | GCG | AAA | GCT | GCC | AAC | CTG | GAC | 1584 |
| Val | Val | Leu | Glu | Arg | Cys | Thr | Glu | Ala | Ala | Lys | Ala | Ala | Asn | Leu | Asp |      |
|     |     | 515 |     |     |     |     | 520 |     |     |     |     | 525 |     |     |     |      |
| TTT | GTC | GAC | TTC | TTG | CCA | CAG | GGT | ATT | CAC | ACG | CGA | ATC | GGT | AAT | GGT | 1632 |
| Phe | Val | Asp | Phe | Leu | Pro | Gln | Gly | Ile | His | Thr | Arg | Ile | Gly | Asn | Gly |      |
|     | 530 |     |     |     |     | 535 |     |     |     |     | 540 |     |     |     |     |      |
| GGC | TAT | ACG | AGT | CTC | TCG | GGT | GGT | CAG | AAC | CAG | AGG | ATT | TGC | TTG | GCT | 1680 |
| Gly | Tyr | Thr | Ser | Leu | Ser | Gly | Gly | Gln | Asn | Gln | Arg | Ile | Cys | Leu | Ala |      |
| 545 |     |     |     |     | 550 |     |     |     |     | 555 |     |     |     |     | 560 |      |
| CGA | GCC | CTG | GTC | AAG | AAG | CCT | GCT | CTA | CTT | CTG | CTA | GAT | GAG | CCG | ACC | 1728 |
| Arg | Ala | Leu | Val | Lys | Lys | Pro | Ala | Leu | Leu | Leu | Leu | Asp | Glu | Pro | Thr |      |
|     |     |     |     | 565 |     |     |     |     | 570 |     |     |     |     | 575 |     |      |
| GCG | GCC | CTC | GAC | GCA | AAC | AGC | GAA | GGA | CTT | ATC | ATG | GAC | GCC | GTC | AAA | 1776 |
| Ala | Ala | Leu | Asp | Ala | Asn | Ser | Glu | Gly | Leu | Ile | Met | Asp | Ala | Val | Lys |      |
|     |     |     | 580 |     |     |     |     | 585 |     |     |     |     | 590 |     |     |      |
| AGC | GTG | GCT | GCC | ACA | GGC | ACA | ACA | GTG | GTC | ATG | GTA | GCG | CAC | CGA | CTC | 1824 |
| Ser | Val | Ala | Ala | Thr | Gly | Thr | Thr | Val | Val | Met | Val | Ala | His | Arg | Leu |      |
|     |     | 595 |     |     |     |     | 600 |     |     |     |     | 605 |     |     |     |      |
| TCC | ACT | GTG | TCA | GAC | TCG | CCC | AAC | ATC | GTG | CTC | ATG | GGT | GCA | GGC | AAG | 1872 |
| Ser | Thr | Val | Ser | Asp | Ser | Pro | Asn | Ile | Val | Leu | Met | Gly | Ala | Gly | Lys |      |
|     | 610 |     |     |     |     | 615 |     |     |     |     | 620 |     |     |     |     |      |
| GTC | ATT | GAG | CAA | GGA | AAC | CAT | GAT | GAA | CTC | ATG | CAG | TTG | GAA | GGC | GCC | 1920 |
| Val | Ile | Glu | Gln | Gly | Asn | His | Asp | Glu | Leu | Met | Gln | Leu | Glu | Gly | Ala |      |
| 625 |     |     |     |     | 630 |     |     |     |     | 635 |     |     |     |     | 640 |      |
| TAC | TTC | AAT | CTT | ATC | CAG | GCG | CAA | CAA | CTA | AAT | GAT | GCA | GAT | GAG | TCA | 1968 |
| Tyr | Phe | Asn | Leu | Ile | Gln | Ala | Gln | Gln | Leu | Asn | Asp | Ala | Asp | Glu | Ser |      |
|     |     |     |     | 645 |     |     |     |     | 650 |     |     |     |     | 655 |     |      |
| TCG | GCA | GAG | GTA | TCT | GCA | GCA | ACC | ACC | AGT | CAA | GTC | ACC | CCA | CAA | AAA | 2016 |
| Ser | Ala | Glu | Val | Ser | Ala | Ala | Thr | Thr | Ser | Gln | Val | Thr | Pro | Gln | Lys |      |
|     |     |     | 660 |     |     |     |     | 665 |     |     |     |     | 670 |     |     |      |
| GCA | AGC | AAG | TCC | GAA | GAT | TCG | GCT | GCT | TCC | AGT | GAC | ACC | GAG | ACG | GTG | 2064 |
| Ala | Ser | Lys | Ser | Glu | Asp | Ser | Ala | Ala | Ser | Ser | Asp | Thr | Glu | Thr | Val |      |
|     |     | 675 |     |     |     |     | 680 |     |     |     |     | 685 |     |     |     |      |
| CCT | CCA | CAG | GCG | AAG | AAG | GAA | GAC | AAG | CCA | GCC | AAA | AAG | GCT | GGA | TTC | 2112 |
| Pro | Pro | Gln | Ala | Lys | Lys | Glu | Asp | Lys | Pro | Ala | Lys | Lys | Ala | Gly | Phe |      |

-continued

|     | 690 |     |     |     |     | 695 |     |     |     |     | 700 |     |     |     |     |      |
|-----|-----|-----|-----|-----|-----|-----|-----|-----|-----|-----|-----|-----|-----|-----|-----|------|
| TGG | AAG | CTC | CTT | TTG | AGA | TGT | TTG | CGT | CTA | GCC | AAA | TCC | GAC | TCG | CCC | 2160 |
| Trp | Lys | Leu | Leu | Leu | Arg | Cys | Leu | Arg | Leu | Ala | Lys | Ser | Asp | Ser | Pro |      |
| 705 |     |     |     |     | 710 |     |     |     |     | 715 |     |     |     |     | 720 |      |
| ATC | ATC | GCT | CTG | GGT | CTC | GCT | GCC | TCA | ATC | GTA | TCG | GGT | GGC | ATC | ATT | 2208 |
| Ile | Ile | Ala | Leu | Gly | Leu | Ala | Ala | Ser | Ile | Val | Ser | Gly | Gly | Ile | Ile |      |
|     |     |     |     | 725 |     |     |     |     | 730 |     |     |     |     | 735 |     |      |
| CTC | GGC | GAA | GCC | ATC | GTC | TTC | GGC | AAC | CTC | ATC | TCG | GTG | CTG | AAC | GAT | 2256 |
| Leu | Gly | Glu | Ala | Ile | Val | Phe | Gly | Asn | Leu | Ile | Ser | Val | Leu | Asn | Asp |      |
|     |     |     | 740 |     |     |     |     | 745 |     |     |     |     | 750 |     |     |      |
| CTC | GAG | AGT | CCA | GAC | TTC | CGA | AGC | AGA | GCA | GAC | CTT | TTC | TCA | CTC | CTC | 2304 |
| Leu | Glu | Ser | Pro | Asp | Phe | Arg | Ser | Arg | Ala | Asp | Leu | Phe | Ser | Leu | Leu |      |
|     |     | 755 |     |     |     |     | 760 |     |     |     |     | 765 |     |     |     |      |
| TTC | TTC | ATA | CTG | GCA | CTC | ATT | GCG | CTC | TTC | TCA | TAC | GCC | GGC | AAT | GGA | 2352 |
| Phe | Phe | Ile | Leu | Ala | Leu | Ile | Ala | Leu | Phe | Ser | Tyr | Ala | Gly | Asn | Gly |      |
|     | 770 |     |     |     |     | 775 |     |     |     |     | 780 |     |     |     |     |      |
| TGC | TGT | TTC | GGT | ATC | GTC | TCT | TCA | CAT | TTT | GTC | GCC | AAA | ATT | CAA | CAT | 2400 |
| Cys | Cys | Phe | Gly | Ile | Val | Ser | Ser | His | Phe | Val | Ala | Lys | Ile | Gln | His |      |
| 785 |     |     |     |     | 790 |     |     |     |     | 795 |     |     |     |     | 800 |      |
| ATC | TCT | CTT | GCT | AGT | ATC | TTG | CGA | CAA | GAT | ATG | CAA | TGG | TTC | TCG | GGC | 2448 |
| Ile | Ser | Leu | Ala | Ser | Ile | Leu | Arg | Gln | Asp | Met | Gln | Trp | Phe | Ser | Gly |      |
|     |     |     |     | 805 |     |     |     |     | 810 |     |     |     |     | 815 |     |      |
| CAG | TCA | GTG | CCT | TCA | CTC | ATG | AGC | AGT | CTC | AGC | TCA | GAT | GCT | GGT | CAG | 2496 |
| Gln | Ser | Val | Pro | Ser | Leu | Met | Ser | Ser | Leu | Ser | Ser | Asp | Ala | Gly | Gln |      |
|     |     |     | 820 |     |     |     |     | 825 |     |     |     |     | 830 |     |     |      |
| CTT | GCT | TGC | TTG | TCC | GGA | GTG | GCT | ATT | GGC | ACC | ATA | TTC | ACG | GTG | TGT | 2544 |
| Leu | Ala | Cys | Leu | Ser | Gly | Val | Ala | Ile | Gly | Thr | Ile | Phe | Thr | Val | Cys |      |
|     |     | 835 |     |     |     |     | 840 |     |     |     |     | 845 |     |     |     |      |
| GTC | TCC | ATC | ACT | GGT | GGT | ATC | ATC | CTT | GCC | CAC | GTG | GTG | GCT | TGG | AAA | 2592 |
| Val | Ser | Ile | Thr | Gly | Gly | Ile | Ile | Leu | Ala | His | Val | Val | Ala | Trp | Lys |      |
|     | 850 |     |     |     |     | 855 |     |     |     |     | 860 |     |     |     |     |      |
| ATT | GCT | GTT | GTC | CTC | CTG | GCT | GCT | GTC | CCC | GTT | ATG | ATC | ACG | GCT | GGC | 2640 |
| Ile | Ala | Val | Val | Leu | Leu | Ala | Ala | Val | Pro | Val | Met | Ile | Thr | Ala | Gly |      |
| 865 |     |     |     |     | 870 |     |     |     |     | 875 |     |     |     |     | 880 |      |
| TAC | GTC | AGA | CTA | CGC | GTG | CTC | GCA | CTC | GCG | GAG | AGT | AGA | CAC | AGA | TCT | 2688 |
| Tyr | Val | Arg | Leu | Arg | Val | Leu | Ala | Leu | Ala | Glu | Ser | Arg | His | Arg | Ser |      |
|     |     |     |     | 885 |     |     |     |     | 890 |     |     |     |     | 895 |     |      |
| GCT | TAC | AAT | GAT | GCT | GCT | TCT | ATC | GCC | GCC | GAG | GCT | TGT | AGA | GGC | ATC | 2736 |
| Ala | Tyr | Asn | Asp | Ala | Ala | Ser | Ile | Ala | Ala | Glu | Ala | Cys | Arg | Gly | Ile |      |
|     |     |     | 900 |     |     |     |     | 905 |     |     |     |     | 910 |     |     |      |
| CGC | ACC | ATT | GCT | TCT | CTC | GGC | AGA | GAG | CGT | GGA | GTG | TCT | AGA | GCA | TCC | 2784 |
| Arg | Thr | Ile | Ala | Ser | Leu | Gly | Arg | Glu | Arg | Gly | Val | Ser | Arg | Ala | Ser |      |
|     |     | 915 |     |     |     |     | 920 |     |     |     |     | 925 |     |     |     |      |
| AAC | GCA | GCG | GTC | AAA | GAG | CCA | TAC | GAC | AAG | GGC | ATC | CGA | TTC | ACC | TTG | 2832 |
| Asn | Ala | Ala | Val | Lys | Glu | Pro | Tyr | Asp | Lys | Gly | Ile | Arg | Phe | Thr | Leu |      |
|     | 930 |     |     |     |     | 935 |     |     |     |     | 940 |     |     |     |     |      |
| ATT | ACC | AAT | ACC | TTG | CTG | GCC | TTG | AGT | TTC | TCA | ATC | ACT | TAC | TTT | GTA | 2880 |
| Ile | Thr | Asn | Thr | Leu | Leu | Ala | Leu | Ser | Phe | Ser | Ile | Thr | Tyr | Phe | Val |      |
| 945 |     |     |     |     | 950 |     |     |     |     | 955 |     |     |     |     | 960 |      |
| TAT | GCC | CTT | GCC | TAC | TGG | TGG | GGA | GCC | AAG | CAA | GTC | AGA | AAT | GGA | ACA | 2928 |
| Tyr | Ala | Leu | Ala | Tyr | Trp | Trp | Gly | Ala | Lys | Gln | Val | Arg | Asn | Gly | Thr |      |
|     |     |     |     | 965 |     |     |     |     | 970 |     |     |     |     | 975 |     |      |
| TAC | AGT | CAA | TTG | GAC | TTT | TTC | ATT | GTT | CTT | CCT | GCT | CTT | CTG | TTC | TCT | 2976 |
| Tyr | Ser | Gln | Leu | Asp | Phe | Phe | Ile | Val | Leu | Pro | Ala | Leu | Leu | Phe | Ser |      |
|     |     |     | 980 |     |     |     |     | 985 |     |     |     |     | 990 |     |     |      |
| GCG | CAG | AGC | GCT | GGA | CAG | ATC | TTC | AGT | CTG | TCA | CCA | GAG | ATG | TCG | CGT | 3024 |
| Ala | Gln | Ser | Ala | Gly | Gln | Ile | Phe | Ser | Leu | Ser | Pro | Glu | Met | Ser | Arg |      |
|     |     | 995 |     |     |     |     | 1000|     |     |     |     | 1005|     |     |     |      |
| GCT | GGT | GTC | GCC | GCT | CGC | AAC | GTC | TTT | GGG | CTA | CAT | GAT | CAG | AAG | CCG | 3072 |
| Ala | Gly | Val | Ala | Ala | Arg | Asn | Val | Phe | Gly | Leu | His | Asp | Gln | Lys | Pro |      |

-continued

|  | 1010 | | | | 1015 | | | | | 1020 | | | | | |  |
|---|---|---|---|---|---|---|---|---|---|---|---|---|---|---|---|---|
| ACC | ATA | GTG | GAT | GTT | GAC | GCG | AAG | CAA | TCT | GGA | GCA | CTG | CCA | AGC | TCG | 3120 |
| Thr | Ile | Val | Asp | Val | Asp | Ala | Lys | Gln | Ser | Gly | Ala | Leu | Pro | Ser | Ser |  |
| 1025 | | | | | 1030 | | | | 1035 | | | | | 1040 | | |
| ACC | TTG | TCT | ATT | CCT | ACT | CTA | GAG | GAC | AAG | GCA | AGT | CCA | TCA | TCT | GGA | 3168 |
| Thr | Leu | Ser | Ile | Pro | Thr | Leu | Glu | Asp | Lys | Ala | Ser | Pro | Ser | Ser | Gly |  |
| | | | | 1045 | | | | 1050 | | | | | 1055 | | | |
| GGC | TGG | ATT | GAG | TTC | AAG | AAC | GTC | AGT | CTA | TGC | TAT | CCG | TCC | AAA | CCT | 3216 |
| Gly | Trp | Ile | Glu | Phe | Lys | Asn | Val | Ser | Leu | Cys | Tyr | Pro | Ser | Lys | Pro |  |
| | | | 1060 | | | | 1065 | | | | 1070 | | | | | |
| CAG | CAC | CCA | GCA | TTG | CAG | AAT | GTC | AAC | ATC | TCC | ATC | AGA | CCA | GGA | GAG | 3264 |
| Gln | His | Pro | Ala | Leu | Gln | Asn | Val | Asn | Ile | Ser | Ile | Arg | Pro | Gly | Glu |  |
| | | 1075 | | | | 1080 | | | | 1085 | | | | | | |
| TTC | ATT | GCA | CTT | GTC | GGC | CCT | AGC | GGA | GCA | GGC | AAG | TCG | ACC | ATT | CTC | 3312 |
| Phe | Ile | Ala | Leu | Val | Gly | Pro | Ser | Gly | Ala | Gly | Lys | Ser | Thr | Ile | Leu |  |
| | 1090 | | | | 1095 | | | | 1100 | | | | | | | |
| TCT | CTG | CTA | CAG | CGC | TTC | TAC | GAT | CCC | ACT | GCT | GGC | AGC | GTA | CAG | CTA | 3360 |
| Ser | Leu | Leu | Gln | Arg | Phe | Tyr | Asp | Pro | Thr | Ala | Gly | Ser | Val | Gln | Leu |  |
| 1105 | | | | 1110 | | | | 1115 | | | | | 1120 | | | |
| GAT | GGG | CAG | GAC | ATC | CGC | GAG | GTT | GCT | GTA | CCA | CAA | CAC | AGA | GGT | CGA | 3408 |
| Asp | Gly | Gln | Asp | Ile | Arg | Glu | Val | Ala | Val | Pro | Gln | His | Arg | Gly | Arg |  |
| | | | | 1125 | | | | 1130 | | | | | 1135 | | | |
| TTG | GGG | CTG | GTA | CCT | CAA | GAG | CCA | GAC | CTC | TTC | CCT | GGC | TCG | ATC | TCC | 3456 |
| Leu | Gly | Leu | Val | Pro | Gln | Glu | Pro | Asp | Leu | Phe | Pro | Gly | Ser | Ile | Ser |  |
| | | | 1140 | | | | 1145 | | | | 1150 | | | | | |
| TAC | AAC | ATC | GGC | TTG | GGC | GCA | GCG | CCA | GGT | CAG | TTG | GTG | ACG | AGA | GAT | 3504 |
| Tyr | Asn | Ile | Gly | Leu | Gly | Ala | Ala | Pro | Gly | Gln | Leu | Val | Thr | Arg | Asp |  |
| | | | 1155 | | | | 1160 | | | | | 1165 | | | | |
| GAT | ATC | GAG | AAG | ATT | TGC | GCA | AAG | TGT | GGC | ATT | CAC | GAG | TTC | ATC | ATG | 3552 |
| Asp | Ile | Glu | Lys | Ile | Cys | Ala | Lys | Cys | Gly | Ile | His | Glu | Phe | Ile | Met |  |
| | | | 1170 | | | | 1175 | | | | 1180 | | | | | |
| AGT | CTG | CCC | GAA | GGC | TAC | AGC | ACA | GAG | TGC | GGC | ACC | AAT | GGT | TCG | AAA | 3600 |
| Ser | Leu | Pro | Glu | Gly | Tyr | Ser | Thr | Glu | Cys | Gly | Thr | Asn | Gly | Ser | Lys |  |
| 1185 | | | | 1190 | | | | 1195 | | | | | 1200 | | | |
| CTC | TCC | GGA | GGT | CAG | AAG | CAA | CGT | ATT | GCT | GTC | GCC | AGA | GCA | TTG | ATC | 3648 |
| Leu | Ser | Gly | Gly | Gln | Lys | Gln | Arg | Ile | Ala | Val | Ala | Arg | Ala | Leu | Ile |  |
| | | | | 1205 | | | | 1210 | | | | | 1215 | | | |
| AGG | TCA | CCG | GAA | GTG | CTT | CTC | CTG | GAC | GAG | TAT | ACA | TCC | GCT | CTG | GAC | 3696 |
| Arg | Ser | Pro | Glu | Val | Leu | Leu | Leu | Asp | Glu | Tyr | Thr | Ser | Ala | Leu | Asp |  |
| | | | 1220 | | | | 1225 | | | | 1230 | | | | | |
| GCC | CAC | TCC | GAG | CAA | CAG | ATC | AAA | GAA | GCA | GTT | GAT | GGA | GCC | AGT | GTG | 3744 |
| Ala | His | Ser | Glu | Gln | Gln | Ile | Lys | Glu | Ala | Val | Asp | Gly | Ala | Ser | Val |  |
| | | 1235 | | | | 1240 | | | | | 1245 | | | | | |
| GAT | CGG | ACT | ACG | ATT | GTG | GTC | GCA | CAT | CGA | TTG | TCC | ACG | GTG | CAG | AAC | 3792 |
| Asp | Arg | Thr | Thr | Ile | Val | Val | Ala | His | Arg | Leu | Ser | Thr | Val | Gln | Asn |  |
| 1250 | | | | | 1255 | | | | 1260 | | | | | | | |
| GCA | GAT | AGA | ATC | TTT | GTG | TTT | GAT | GAT | GGA | CGT | GTG | GTG | GAG | GTT | GGT | 3840 |
| Ala | Asp | Arg | Ile | Phe | Val | Phe | Asp | Asp | Gly | Arg | Val | Val | Glu | Val | Gly |  |
| 1265 | | | | 1270 | | | | 1275 | | | | | 1280 | | | |
| AGC | CAT | GCT | GAG | CTT | GTT | GCT | CAA | GGG | GGT | TTG | TAT | GCA | GGC | ATG | GTT | 3888 |
| Ser | His | Ala | Glu | Leu | Val | Ala | Gln | Gly | Gly | Leu | Tyr | Ala | Gly | Met | Val |  |
| | | | | 1285 | | | | 1290 | | | | | 1295 | | | |
| CTG | GCG | CAG | ACA | CTC | ACA | TGA | | | | | | | | | | 3909 |
| Leu | Ala | Gln | Thr | Leu | Thr | | | | | | | | | | | |
| | | | 1300 | | | | | | | | | | | | | |

( 2 ) INFORMATION FOR SEQ ID NO:2:

( i ) SEQUENCE CHARACTERISTICS:
        ( A ) LENGTH: 1302 amino acids
        ( B ) TYPE: amino acid ( D ) TOPOLOGY: linear ( i i ) MOLECULE TYPE: protein ( x i ) SEQUENCE DESCRIPTION: SEQ ID NO:2:

| Met | Ser | Ser | Ala | Asp | Gly | Arg | Arg | Thr | Val | Ser | Ser | Asp | Tyr | Gly | His |
|---|---|---|---|---|---|---|---|---|---|---|---|---|---|---|---|
| 1 | | | | 5 | | | | | 10 | | | | | 15 | |
| Pro | Arg | Pro | Ser | Met | Ala | Asn | Val | Glu | Ala | Asp | His | Asn | Phe | Glu | Thr |
| | | | 20 | | | | | 25 | | | | | 30 | | |
| Thr | Thr | Leu | Asn | Ser | Ala | Gln | Pro | Arg | Ser | Trp | His | Thr | Glu | Phe | Val |
| | | 35 | | | | | 40 | | | | | 45 | | | |
| Phe | Val | Ser | Arg | Lys | Leu | Ile | Gln | Gln | Ile | Leu | Gly | Lys | Asn | Pro | Phe |
| | 50 | | | | | 55 | | | | | 60 | | | | |
| Lys | Ser | Ser | Tyr | Leu | Asp | Leu | Phe | Lys | Leu | Val | Asn | Asp | Ala | Lys | Ser |
| 65 | | | | | 70 | | | | | 75 | | | | | 80 |
| Lys | Ala | Val | Leu | Trp | Ala | Gly | Ile | Leu | Leu | Ala | Ile | Ala | Ala | Gly | Cys |
| | | | | 85 | | | | | 90 | | | | | 95 | |
| Pro | Leu | Pro | Ile | Ile | Gly | Tyr | Ile | Phe | Gly | Gln | Ile | Ile | Thr | Ser | Phe |
| | | | 100 | | | | | 105 | | | | | 110 | | |
| Pro | Pro | Pro | Glu | Asp | Val | Leu | Arg | Asp | Arg | Leu | Tyr | Gln | Leu | Val | Gly |
| | | | 115 | | | | | 120 | | | | | 125 | | |
| Val | Ala | Cys | Gly | Tyr | Phe | Ile | Val | Thr | Thr | Gly | Tyr | Ala | Ile | Ala | Trp |
| | 130 | | | | | 135 | | | | | 140 | | | | |
| Gly | Leu | Thr | Gly | Glu | Lys | Ile | Ser | Arg | Arg | Phe | Arg | Glu | Thr | Leu | Val |
| 145 | | | | | 150 | | | | | 155 | | | | | 160 |
| Glu | Arg | Leu | Leu | Gly | Leu | Glu | Gln | Ala | Tyr | Phe | Asp | Ile | Lys | Asp | Pro |
| | | | | 165 | | | | | 170 | | | | | 175 | |
| Asp | Ile | Thr | Asn | Leu | Leu | Thr | Glu | Lys | Ile | Glu | Ala | Ile | Gln | Ile | Gly |
| | | | 180 | | | | | 185 | | | | | 190 | | |
| Thr | Ser | Glu | Lys | Val | Gly | Ile | Phe | Ile | Gln | Ser | Ile | Ser | Tyr | Phe | Val |
| | | 195 | | | | | 200 | | | | | 205 | | | |
| Ala | Ala | Phe | Ile | Val | Gly | Phe | Ile | Leu | Asn | Ala | Lys | Leu | Thr | Gly | Ile |
| | 210 | | | | | 215 | | | | | 220 | | | | |
| Leu | Phe | Ala | Ala | Val | Ile | Pro | Leu | Met | Ala | Leu | Ile | Val | Thr | Val | Gly |
| 225 | | | | | 230 | | | | | 235 | | | | | 240 |
| Ser | Ser | Arg | Ile | Ala | Lys | Tyr | Thr | Lys | Ala | Ala | Thr | Glu | Tyr | Thr | Glu |
| | | | | 245 | | | | | 250 | | | | | 255 | |
| Ala | Ala | Gly | Arg | Ile | Ala | Glu | Ser | Ala | Ile | His | Ala | Val | Lys | Val | Val |
| | | | 260 | | | | | 265 | | | | | 270 | | |
| Gln | Ala | Phe | Gly | Met | Ala | Glu | Asn | Leu | Ser | Lys | Glu | His | Tyr | Arg | Leu |
| | | 275 | | | | | 280 | | | | | 285 | | | |
| Leu | Lys | Leu | Ser | Ala | Arg | Tyr | Ala | Ile | Arg | Lys | Ser | Val | Ser | Ala | Ala |
| | 290 | | | | | 295 | | | | | 300 | | | | |
| Phe | Met | Leu | Gly | Leu | Val | Tyr | Phe | Thr | Ala | Tyr | Ser | Ala | Asn | Ala | Leu |
| 305 | | | | | 310 | | | | | 315 | | | | | 320 |
| Ala | Phe | Trp | Glu | Gly | Ser | Arg | Leu | Ala | Ala | Glu | Ser | Gly | Ser | Asn | Asn |
| | | | | 325 | | | | | 330 | | | | | 335 | |
| Ala | Gly | Thr | Val | Tyr | Ala | Val | Val | Phe | Leu | Ile | Ile | Asp | Ala | Ser | Phe |
| | | | 340 | | | | | 345 | | | | | 350 | | |
| Val | Val | Gly | Gln | Phe | Gly | Pro | Phe | Leu | Gly | Ser | Phe | Ala | Thr | Ala | Ala |
| | | 355 | | | | | 360 | | | | | 365 | | | |
| Ala | Ala | Gly | Glu | Ser | Val | Tyr | Glu | Ile | Leu | Asn | His | Pro | Gln | Ser | Glu |
| | 370 | | | | | 375 | | | | | 380 | | | | |
| Ile | Asn | Val | Tyr | Ser | Glu | Ala | Gly | Gln | Glu | Ala | Thr | Glu | Ser | Asp | Met |
| 385 | | | | | 390 | | | | | 395 | | | | | 400 |

```
Lys  Ala  Asp  Leu  Val  Phe  Arg  Asn  Val  Thr  Phe  Val  Tyr  Pro  Ala  Arg
               405                      410                     415

Thr  Ser  Ala  Arg  Ala  Leu  Glu  Glu  Met  Ser  Leu  Ile  Leu  Lys  Ala  Gly
               420                      425                     430

Gln  Met  Asn  Ala  Ile  Val  Gly  Thr  Ser  Gly  Cys  Gly  Lys  Ser  Thr  Leu
          435                      440                     445

Val  Ser  Leu  Leu  Leu  Arg  Leu  Tyr  Asp  Ile  Ser  Ser  Gly  Gln  Leu  Thr
     450                      455                     460

Ile  Gly  Ser  His  Asp  Ile  Lys  Asp  Phe  Asn  Val  Arg  Ser  Leu  Arg  Lys
465                      470                     475                     480

Tyr  Thr  Ala  Leu  Val  Asp  Gln  Asp  Ser  Val  Leu  Phe  Ser  Gly  Ser  Val
               485                      490                     495

Leu  Glu  Asn  Ile  Ser  Tyr  Gly  Leu  Gly  Glu  His  Ser  Leu  Ser  Asp  Asp
          500                      505                     510

Val  Val  Leu  Glu  Arg  Cys  Thr  Glu  Ala  Ala  Lys  Ala  Ala  Asn  Leu  Asp
          515                      520                     525

Phe  Val  Asp  Phe  Leu  Pro  Gln  Gly  Ile  His  Thr  Arg  Ile  Gly  Asn  Gly
     530                      535                     540

Gly  Tyr  Thr  Ser  Leu  Ser  Gly  Gly  Gln  Asn  Gln  Arg  Ile  Cys  Leu  Ala
545                      550                     555                     560

Arg  Ala  Leu  Val  Lys  Lys  Pro  Ala  Leu  Leu  Leu  Leu  Asp  Glu  Pro  Thr
               565                      570                     575

Ala  Ala  Leu  Asp  Ala  Asn  Ser  Glu  Gly  Leu  Ile  Met  Asp  Ala  Val  Lys
               580                      585                     590

Ser  Val  Ala  Ala  Thr  Gly  Thr  Thr  Val  Val  Met  Val  Ala  His  Arg  Leu
          595                      600                     605

Ser  Thr  Val  Ser  Asp  Ser  Pro  Asn  Ile  Val  Leu  Met  Gly  Ala  Gly  Lys
     610                      615                     620

Val  Ile  Glu  Gln  Gly  Asn  His  Asp  Glu  Leu  Met  Gln  Leu  Glu  Gly  Ala
625                      630                     635                     640

Tyr  Phe  Asn  Leu  Ile  Gln  Ala  Gln  Gln  Leu  Asn  Asp  Ala  Asp  Glu  Ser
               645                      650                     655

Ser  Ala  Glu  Val  Ser  Ala  Ala  Thr  Thr  Ser  Gln  Val  Thr  Pro  Gln  Lys
               660                      665                     670

Ala  Ser  Lys  Ser  Glu  Asp  Ser  Ala  Ala  Ser  Ser  Asp  Thr  Glu  Thr  Val
          675                      680                     685

Pro  Pro  Gln  Ala  Lys  Lys  Glu  Asp  Lys  Pro  Ala  Lys  Lys  Ala  Gly  Phe
     690                      695                     700

Trp  Lys  Leu  Leu  Leu  Arg  Cys  Leu  Arg  Leu  Ala  Lys  Ser  Asp  Ser  Pro
705                      710                     715                     720

Ile  Ile  Ala  Leu  Gly  Leu  Ala  Ala  Ser  Ile  Val  Ser  Gly  Gly  Ile  Ile
               725                      730                     735

Leu  Gly  Glu  Ala  Ile  Val  Phe  Gly  Asn  Leu  Ile  Ser  Val  Leu  Asn  Asp
               740                      745                     750

Leu  Glu  Ser  Pro  Asp  Phe  Arg  Ser  Arg  Ala  Asp  Leu  Phe  Ser  Leu  Leu
          755                      760                     765

Phe  Phe  Ile  Leu  Ala  Leu  Ile  Ala  Leu  Phe  Ser  Tyr  Ala  Gly  Asn  Gly
     770                      775                     780

Cys  Cys  Phe  Gly  Ile  Val  Ser  Ser  His  Phe  Val  Ala  Lys  Ile  Gln  His
785                      790                     795                     800

Ile  Ser  Leu  Ala  Ser  Ile  Leu  Arg  Gln  Asp  Met  Gln  Trp  Phe  Ser  Gly
               805                      810                     815

Gln  Ser  Val  Pro  Ser  Leu  Met  Ser  Ser  Leu  Ser  Ser  Asp  Ala  Gly  Gln
```

|     |     |     |     |     | 820 |     |     |     |     | 825 |     |     |     |     | 830 |     |
| --- | --- | --- | --- | --- | --- | --- | --- | --- | --- | --- | --- | --- | --- | --- | --- | --- |
| Leu | Ala | Cys<br>835 | Leu | Ser | Gly | Val | Ala<br>840 | Ile | Gly | Thr | Ile | Phe<br>845 | Thr | Val | Cys |
| Val | Ser | Ile<br>850 | Thr | Gly | Gly | Ile<br>855 | Ile | Leu | Ala | His | Val<br>860 | Val | Ala | Trp | Lys |
| Ile<br>865 | Ala | Val | Val | Leu<br>870 | Leu | Ala | Ala | Val | Pro<br>875 | Val | Met | Ile | Thr | Ala | Gly<br>880 |
| Tyr | Val | Arg | Leu | Arg<br>885 | Val | Leu | Ala | Leu<br>890 | Ala | Glu | Ser | Arg | His<br>895 | Arg | Ser |
| Ala | Tyr | Asn | Asp<br>900 | Ala | Ala | Ser | Ile<br>905 | Ala | Ala | Glu | Ala | Cys<br>910 | Arg | Gly | Ile |
| Arg | Thr | Ile<br>915 | Ala | Ser | Leu | Gly | Arg<br>920 | Glu | Arg | Gly | Val | Ser<br>925 | Arg | Ala | Ser |
| Asn | Ala<br>930 | Ala | Val | Lys | Glu | Pro<br>935 | Tyr | Asp | Lys | Gly | Ile<br>940 | Arg | Phe | Thr | Leu |
| Ile<br>945 | Thr | Asn | Thr | Leu | Leu<br>950 | Ala | Leu | Ser | Phe | Ser<br>955 | Ile | Thr | Tyr | Phe | Val<br>960 |
| Tyr | Ala | Leu | Ala | Tyr<br>965 | Trp | Trp | Gly | Ala | Lys<br>970 | Gln | Val | Arg | Asn | Gly<br>975 | Thr |
| Tyr | Ser | Gln | Leu<br>980 | Asp | Phe | Phe | Ile | Val<br>985 | Leu | Pro | Ala | Leu | Leu<br>990 | Phe | Ser |
| Ala | Gln | Ser<br>995 | Ala | Gly | Gln | Ile | Phe<br>1000 | Ser | Leu | Ser | Pro | Glu<br>1005 | Met | Ser | Arg |
| Ala | Gly | Val<br>1010 | Ala | Ala | Arg | Asn | Val<br>1015 | Phe | Gly | Leu | His | Asp<br>1020 | Gln | Lys | Pro |
| Thr<br>1025 | Ile | Val | Asp | Val | Asp<br>1030 | Ala | Lys | Gln | Ser | Gly<br>1035 | Ala | Leu | Pro | Ser | Ser<br>1040 |
| Thr | Leu | Ser | Ile | Pro<br>1045 | Thr | Leu | Glu | Asp | Lys<br>1050 | Ala | Ser | Pro | Ser | Ser<br>1055 | Gly |
| Gly | Trp | Ile | Glu | Phe<br>1060 | Lys | Asn | Val | Ser | Leu<br>1065 | Cys | Tyr | Pro | Ser | Lys<br>1070 | Pro |
| Gln | His | Pro<br>1075 | Ala | Leu | Gln | Asn | Val<br>1080 | Asn | Ile | Ser | Ile | Arg<br>1085 | Pro | Gly | Glu |
| Phe | Ile | Ala<br>1090 | Leu | Val | Gly | Pro<br>1095 | Ser | Gly | Ala | Gly | Lys<br>1100 | Ser | Thr | Ile | Leu |
| Ser<br>1105 | Leu | Leu | Gln | Arg | Phe<br>1110 | Tyr | Asp | Pro | Thr | Ala<br>1115 | Gly | Ser | Val | Gln | Leu<br>1120 |
| Asp | Gly | Gln | Asp | Ile<br>1125 | Arg | Glu | Val | Ala | Val<br>1130 | Pro | Gln | His | Arg | Gly<br>1135 | Arg |
| Leu | Gly | Leu | Val | Pro<br>1140 | Gln | Glu | Pro | Asp | Leu<br>1145 | Phe | Pro | Gly | Ser | Ile<br>1150 | Ser |
| Tyr | Asn | Ile | Gly | Leu<br>1155 | Gly | Ala | Ala | Pro | Gly<br>1160 | Gln | Leu | Val | Thr | Arg<br>1165 | Asp |
| Asp | Ile | Glu | Lys<br>1170 | Ile | Cys | Ala | Lys<br>1175 | Cys | Gly | Ile | His | Glu<br>1180 | Phe | Ile | Met |
| Ser<br>1185 | Leu | Pro | Glu | Gly | Tyr<br>1190 | Ser | Thr | Glu | Cys | Gly<br>1195 | Thr | Asn | Gly | Ser | Lys<br>1200 |
| Leu | Ser | Gly | Gly | Gln<br>1205 | Lys | Gln | Arg | Ile | Ala<br>1210 | Val | Ala | Arg | Ala | Leu<br>1215 | Ile |
| Arg | Ser | Pro | Glu | Val<br>1220 | Leu | Leu | Leu | Asp | Glu<br>1225 | Tyr | Thr | Ser | Ala | Leu<br>1230 | Asp |
| Ala | His | Ser<br>1235 | Glu | Gln | Gln | Ile | Lys<br>1240 | Glu | Ala | Val | Asp | Gly<br>1245 | Ala | Ser | Val |

| | | | | | | | | | | | | | | |
|---|---|---|---|---|---|---|---|---|---|---|---|---|---|---|
| Asp | Arg | Thr | Thr | Ile | Val | Val | Ala | His | Arg | Leu | Ser | Thr | Val | Gln | Asn |
| | | 1250 | | | | 1255 | | | | 1260 | | | | | |
| Ala | Asp | Arg | Ile | Phe | Val | Phe | Asp | Asp | Gly | Arg | Val | Val | Glu | Val | Gly |
| 1265 | | | | | 1270 | | | | | 1275 | | | | | 1280 |
| Ser | His | Ala | Glu | Leu | Val | Ala | Gln | Gly | Gly | Leu | Tyr | Ala | Gly | Met | Val |
| | | | | 1285 | | | | | 1290 | | | | | 1295 | |
| Leu | Ala | Gln | Thr | Leu | Thr | | | | | | | | | | |
| | | | 1300 | | | | | | | | | | | | |

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:3:

ACGCGAGATC TTCTCTCCAG TCAATCCCCA CGCAATTGC      39

( 2 ) INFORMATION FOR SEQ ID NO:4:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:4:

CCTGCGTCAT CTTCAAGGGC GAGCTCATTC GGGTTCAAGA ATCTTC      46

MULTIPLE DRUG RESISTANCE GENE OF *AUREOBASIDIUM PULLULANS*

TECHNICAL FIELD OF THE INVENTION

This invention relates to recombinant DNA technology. In particular, the invention concerns the cloning of nucleic acid encoding the multiple drug resistance protein of *Aureobasidium pullulans*.

BACKGROUND OF THE INVENTION

Multiple drug resistance (MDR) mediated by the human mdr-1 gene product was initially recognized during the course of developing regimens for cancer chemotherapy (Fojo et al., 1987, *Journal of Clinical Oncology* 5:1922–1927). A multiple drug resistant cancer cell line exhibits resistance to high levels of a large variety of cytotoxic compounds. Frequently these cytotoxic compounds will have no common structural features nor will they interact with a common target within the cell. Resistance to these cytotoxic agents is mediated by an outward directed, ATP-dependent pump encoded by the mdr-1 gene. By this mechanism, toxic levels of a particular cytotoxic compound are not allowed to accumulate within the cell.

MDR-like genes have been identified in a number of divergent organisms including numerous bacterial species, the fruit fly *Drosophila melanogaster, Plasmodium falciparum*, the yeast *Saccharomyces cerevisiae, Caenorhabditis elegans, Leishmania donovanii,* marine sponges, the plant *Arabidopsis thaliana,* as well as *Homo sapiens.* Extensive searches have revealed several classes of compounds that are able to reverse the MDR phenotype of multiple drug resistant human cancer cell lines rendering them susceptible to the effects of cytotoxic compounds. These compounds, referred to herein as "MDR inhibitors", include for example, calcium channel blockers, anti-arrhythmics, antihypertensives, antibiotics, antihistamines, immuno-suppressants, steroid hormones, modified steroids, lipophilic cations, diterpenes, detergents, antidepressants, and antipsychotics (Gottesman and Pastan, 1993, *Annual Review of Biochemistry* 62:385–427). Clinical application of human MDR inhibitors to cancer chemotherapy has become an area of intensive focus for research.

On another front, the discovery and development of antifungal compounds for specific fungal species has also met with some degree of success. Candida species represent the majority of fungal infections, and screens for new antifungal compounds have been designed to discover anti-Candida compounds. During development of antifungal agents, activity has generally been optimized based on activity against *C. albicans.* As a consequence, these anti-Candida compounds frequently do not possess clinically significant activity against other fungal species. However, it is interesting to note that at higher concentrations some anti-Candida compounds are able to kill other fungal species. This suggests that the antifungal target(s) of these anti-Candida compounds is present in these fungal species as well. Such results indicate that some fungal species possess a natural mechanism of resistance that permits them to survive in clinically relevant concentrations of antifungal compounds. Such a general mechanism of resistance to antifungal compounds in the fungi has remained undescribed.

SUMMARY OF THE INVENTION

The present invention describes the discovery of an MDR gene in the fungus *Aureobasidium pullulans*. The protein encoded by this gene, hereinafter "AP-MDR", provides the MDR phenotype. The invention provides isolated nucleic acid sequences that encode the AP-MDR. These nucleic acid sequences include the natural DNA (deoxyribonucleic acid) coding sequence (presented as a part of SEQ ID NO: 1 of the Sequence Listing) as well as any other isolated nucleic acid compound that encodes AP-MDR. Included in this invention are vectors and host cells that comprise nucleic acid sequences encoding AP-MDR. The present invention further provides AP-MDR in purified form. The amino acid sequence of AP-MDR is provided in the Sequence Listing as SEQ ID NO: 2.

In another embodiment, the invention provides a method for determining the fungal MDR inhibition activity of a compound which comprises:

a) growing a culture of yeast cells, transformed with a vector which provides expression of the AP-MDR, in the presence of:

(i) an antifungal agent to which said yeast cell is resistant, but to which said yeast cell is sensitive in its untransformed state;

(ii) a compound suspected of possessing fungal MDR inhibition activity; and b) determining the fungal MDR inhibition activity of said compound by measuring the ability of the antifungal agent to inhibit the growth of said yeast cell.

BRIEF DESCRIPTION OF THE FIGURE

The restriction enzyme site and function map presented in the accompanying drawing is an approximate representation of plasmid pPSR3, discussed herein. The restriction enzyme site information is not exhaustive. There may be more restriction enzyme sites of a given type on the vector than actually shown on the map.

DETAILED DESCRIPTION OF THE INVENTION

As used herein, the term "AP-MDR" means the multiple drug resistance protein of *Aureobasidium pullulans*.

The term "vector" refers to any autonomously replicating or integrating agent, including but not limited to plasmids and viruses (including phage), comprising a deoxyribonucleic acid (DNA) molecule to which one or more additional DNA molecules can be added. Included in this definition is the term "expression vector". Vectors are used either to amplify and/or to express DNA or RNA which encodes AP-MDR, or to amplify DNA or RNA that hybridizes with DNA or RNA encoding AP-MDR.

The term "expression vector" refers to vectors which comprise a transcriptional promoter (hereinafter "promoter") and other regulatory sequences positioned to drive expression of a DNA segment that encodes AP-MDR. Expression vectors of the present invention are replicable DNA constructs in which a DNA sequence encoding AP-MDR is operably linked to suitable control sequences capable of effecting the expression of AP-MDR in a suitable host. Such control sequences include a promoter, an optional operator sequence to control transcription, a sequence encoding suitable mRNA ribosomal binding sites, and sequences which control termination of transcription and translation. DNA regions are operably linked when they are functionally related to each other. For example, a promoter is operably linked to a DNA coding sequence if it controls the transcription of the sequence, or a ribosome binding site is operably linked to a coding sequence if it is positioned so as to permit translation.

The term "MDR inhibition activity" refers to the ability of a compound to inhibit the MDR activity of a host cell, thereby increasing the antifungal activity of an antifungal compound against said host cell.

In the present invention, AP-MDR may be synthesized by host cells transformed with vectors that provide for the expression of DNA encoding AP-MDR. The DNA encoding AP-MDR may be the natural sequence or a synthetic sequence or a combination of both ("semisynthetic sequence"). The in vitro or in vivo transcription and translation of these sequences results in the production of AP-MDR. Synthetic and semi-synthetic sequences encoding AP-MDR may be constructed by techniques well known in the art. See Brown et al. (1979) *Methods in Enzymology*, Academic Press, N.Y., 68:109– 151. AP-MDR-encoding DNA, or portions thereof, may be generated using a conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

Owing to the natural degeneracy of the genetic code, the skilled artisan will recognize that a sizable yet definite number of DNA sequences may be constructed which encode AP-MDR. All such DNA sequences are provided by the present invention. A preferred DNA coding sequence encoding AP-MDR is the natural sequence of *Aureobasidium pullulans* (SEQ. ID. NO:1). This DNA sequence is preferably obtained from plasmid pPSR3. Plasmid pPSR3 can be obtained from the host cell *Escherichia coli* XL1-Blue/pPSR3 which was deposited in the permanent culture collection of the Northern Regional Research Laboratory (NRRL), United States Department of Agriculture Service, 1815 North University Street, Peoria, Ill. 61604, on Feb. 23, 1994, and is available under accession number NRRL B-21202. A restriction site and function map of pPSR3 is provided as FIG. 1 of the drawings. The DNA encoding AP-MDR can be obtained from plasmid pPSR3 on an approximately 4.0 kilobase pair SacI-SphI restriction enzyme fragment.

To effect the translation of AP-MDR encoding DNA, one inserts the natural, synthetic, or semi-synthetic AP-MDR-encoding DNA sequence into any of a large number of appropriate expression vectors through the use of appropriate restriction endonucleases and DNA ligases. Synthetic and semi-synthetic AP-MDR encoding DNA sequences can be designed, and natural AP-MDR encoding nucleic acid can be modified, to possess restriction endonuclease cleavage sites to facilitate isolation from and integration into these vectors. Particular restriction endonucleases employed will be dictated by the restriction endonuclease cleavage pattern of the expression vector utilized. Restriction enzyme sites are chosen so as to properly orient the AP-MDR encoding DNA with the control sequences to achieve proper in-frame transcription and translation of the AP-MDR molecule. The AP-MDR encoding DNA must be positioned so as to be in proper reading frame with the promoter and ribosome binding site of the expression vector, both of which are functional in the host cell in which AP-MDR is to be expressed.

Expression of AP-MDR in yeast cells, such as *Saccharomyces cerevisiae* is preferred. Suitable promoter sequences for use with yeast hosts include the promoters for 3-phosphoglycerate kinase (found on plasmid pAP12BD ATCC 53231 and described in U.S. Pat. No. 4,935,350, Jun. 19, 1990) or other glycolytic enzymes such as enolase (found on plasmid pAC1 ATCC 39532), glyceraldehyde-3-phosphate dehydrogenase (derived from plasmid pHcGAPC1 ATCC 57090, 57091), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Inducible yeast promoters have the additional advantage of transcription controlled by growth conditions. Such promoters include the promoter regions for alcohol dehydrogenase 2, isocytochrome C, acid phosphotase, degradative enzymes associated with nitrogen metabolism, metallothionein (contained on plasmid vector pCL28XhoLHBPV ATCC 39475, U.S. Pat. No. 4,840,896), glyceraldehyde 3-phosphate dehydrogenase, and enzymes responsible for maltose and galactose utilization (GAL1 found on plasmid pRY121 ATCC 37658 and on plasmid pPSR3). Suitable vectors and promoters for use in yeast expression are further described by R. Hitzeman et al., in European Patent Publication No. 73,657A. Yeast enhancers such as the UAS Gal enhancer from *Saccharomyces cerevisiae* (found in conjunction with the CYC1 promoter on plasmid YEpsec—hI1beta, ATCC 67024), also are advantageously used with yeast promoters.

A variety of expression vectors useful in the present invention are well known in the art. For expression in Saccharomyces, the plasmid YRp7, for example, (ATCC-40053, Stinchcomb, et al., 1979, *Nature* 282:39; Kingsman et al., 1979, *Gene* 7:141; Tschemper et al., 1980, *Gene* 10:157) is commonly used. This plasmid contains the trp gene which provides a selection marker for a mutant strain of yeast lacking the ability to grow in tryptophan, for example ATCC no. 44076 or PEP4-1 (Jones, 1977, *Genetics* 85:12).

A preferred vector for expression of AP-MDR in a *Saccharomyces cerevisiae* host cell is plasmid pPSR3. Plasmid pPSR3 is derived from *S. cerevisiae* plasmid pYES-2, which comprises the *S. cerevisiae* GAL1 promoter region. Plasmid pYES-2 is publicly available from Invitrogen Corp., Sorrento Valley Blvd., San Diego Calif. 92121, under catalog #825-20. The plasmid pPSR3 was constructed in the following manner. Genomic DNA was isolated from *Aureobasidium pullulans* and then partially digested with the restriction enzyme Sau3AI. The partially digested DNA was ligated into the cosmid cloning vector SuperCos 1 (Stratagene, LaJolla Calif. 92037). One of the cosmid clones, cR106-20A, contained a DNA fragment having high sequence homology with the human mdr-1 gene. Cosmid cR106-20A was digested with the restriction endonucleases BstXI and SphI. This digestion released an approximately 4,500 base pair DNA fragment containing the entire AP-MDR open reading frame and the AP-MDR promoter. This approximately 4,500 base pair DNA fragment was gel purified using standard procedures. Plasmid pYES-2 was also digested with BstXI and SphI and the approximately 4,500 base pair BstXI-SphI DNA fragment containing the AP-MDR gene was ligated to this vector to form an intermediate plasmid. The intermediate plasmid was then digested with EcoRI and SacI to remove the *Aureobasidium pullulans* AP-MDR promoter region. The desired vector fragment containing the AP-MDR open reading frame was gel purified away from the fragment released by restriction endonuclease digestion. The deleted region was replaced with a polymerase chain reaction (PCR) DNA fragment which juxtaposed the AP-MDR open reading frame with the

*Saccharomyces cerevisiae* GAL1 promoter of the intermediate plasmid originating from plasmid pYES-2.

The PCR fragment was generated using cosmid cR106-20A as template with the following primers:

5'-ACGCGAGATCTTCTCTCCAGTCAATC-CCCACGCAATTGC-3' (SEQ. ID. NO: 3); and

5'-CCTGCGTCATCTTCAAGGGCGAGCTCAT-TCGGGTTCAAGAATCTTC-3' (SEQ. ID. NO: 4). The PCR fragment was digested with SacI and EcoRI and gel purified. The gel purified fragment was then ligated to the EcoRI-SacI digested intermediate plasmid described above. This process brought the AP-MDR open reading frame into proper alignment with the GAL1 promoter of *S. cerevisiae*. The resulting plasmid was called pPSR3. Plasmid pPSR3 is useful for the expression of the AP-MDR in *S. cerevisiae*.

Figure 1:
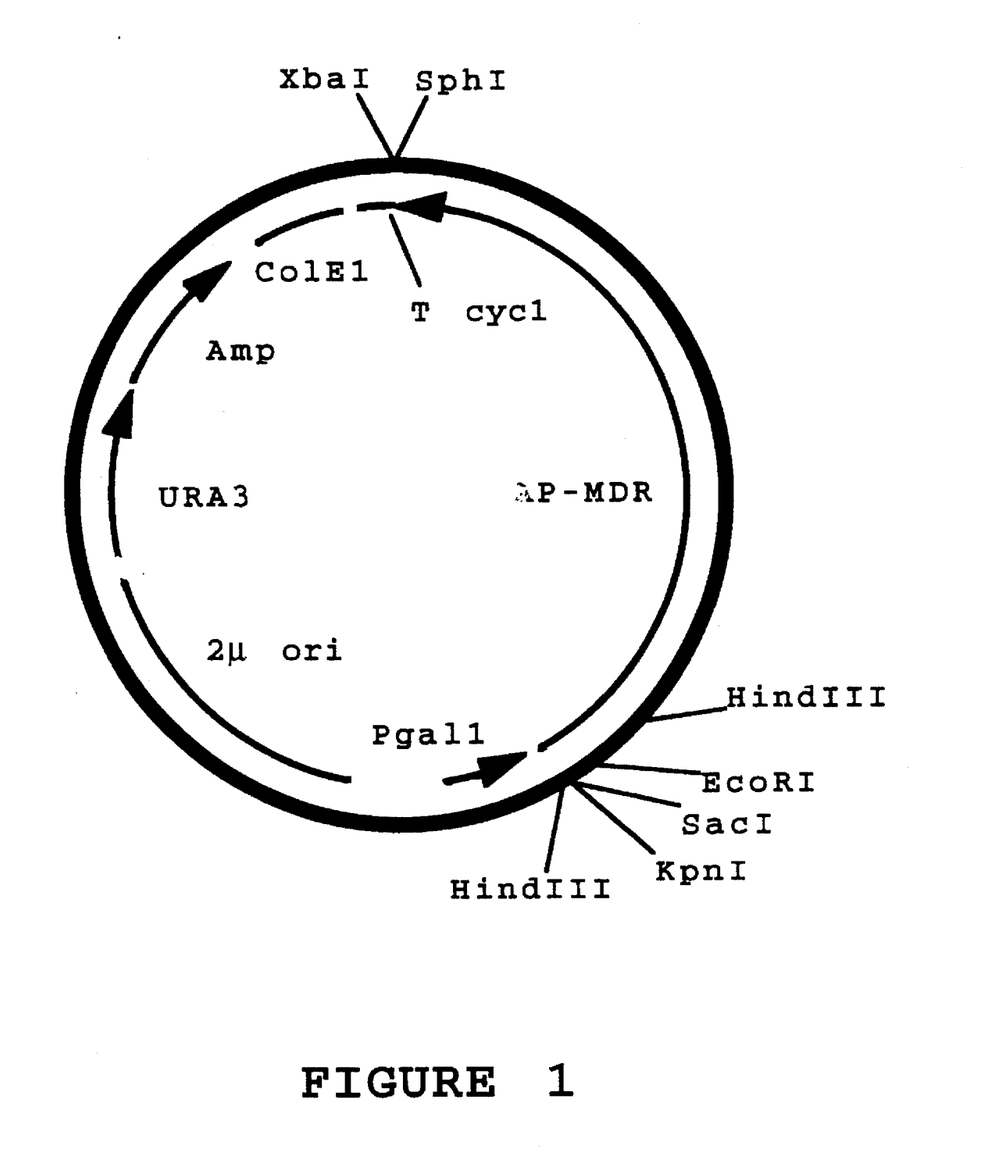
FIG. 1—A restriction enzyme site and function map of plasmid pPSR3.

A representation of plasmid pPSR3 is provided as FIG. 1. As noted above, this plasmid contains the AP-MDR encoding DNA operably linked to the *Saccharomyces cerevisiae* GAL1 promoter (Pgal1). Plasmid pPSR3 also comprises the yeast transcription terminator cyc 1 (T cyc 1) located in a position 3' to the AP-MDR encoding DNA. Plasmid pPSR3 further comprises the ColE1 origin of replication (ColE1 ori) which allows replication in *Escherichia coli* host cells, and the ampicillin resistance gene (Amp) for selection of *E. coli* cells transformed with the plasmid grown in the presence of ampicillin. Plasmid pPSR3 further comprises the yeast 2μ origin of replication (2μ ori) allowing replication in yeast host cells, and the yeast URA3 gene for selection of *S. cerevisiae* cells transformed with the plasmid grown in a medium lacking uracil.

The present invention also comprises a method for constructing a recombinant host cell capable of expressing AP-MDR, said method comprising transforming a host cell with a recombinant DNA vector that comprises an isolated DNA sequence encoding AP-MDR. The present invention further comprises a method for expressing AP-MDR in a recombinant host cell transformed with a vector capable of providing expression of AP-MDR; said method comprising culturing said transformed host cell under conditions suitable for expression.

In a preferred embodiment of the invention *Saccharomyces cerevisiae* INVSc1 or INVSc2 cells (available from Invitrogen Corp., Sorrenno Valley Blvd., San Diego Calif. 92121) are employed as host cells, but numerous other cell lines are available for this use. The transformed host cells are plated on an appropriate medium under selective pressure (minimal medium lacking uracil). The cultures are then incubated for a time and temperature appropriate to the host cell line employed.

The techniques involved in the transformation of yeast cells such as *Saccharomyces cerevisiae* cells are well known in the art and may be found in such general references as Ausubel et al., *Current Protocols in Molecular Biology* (1989), John Wiley & Sons, New York, N.Y. and supplements. The precise conditions under which the transformed yeast cells are cultured is dependent upon the nature of the yeast host cell line and the vectors employed.

AP-MDR may be isolated and purified from transformed host cells by general techniques of membrane-bound protein isolation and purification which are well-known to those of ordinary skill in the art. Isolated AP-MDR is useful in structure-based drug design studies, in vitro binding assays, and production of polyclonal or monoctonal antibodies.

An alternative to recombinant DNA production of AP-MDR is synthesis by solid phase peptide synthesis. This method is described in U.S. Pat. No. 4,617,149, the entire teaching of which is incorporated herein by reference. The principles of solid phase chemical synthesis of polypeptides are well known in the art and may be found in general texts in the area such as Dugas, H. and Penney, C., *Bioorganic Chemistry* (1981), Springer-Verlag, New York, pages 54–92. However, recombinant methods are preferred.

Nucleic acid, either RNA or DNA, which encodes AP-MDR, or a portion thereof, is also useful in producing nucleic acid molecules useful in diagnostic assays for the detection of AP-MDR mRNA, AP-MDR cDNA (complementary DNA), or genomic DNA. Further, nucleic acid, either RNA or DNA, which does not encode AP-MDR, but which nonetheless is capable of hybridizing with AP-MDR-encoding DNA or RNA is also useful in such diagnostic assays. These nucleic acid molecules may be covalently labeled by known methods with a detectable moiety such as a fluorescent group, a radioactive atom or a chemiluminescent group. The labeled nucleic acid is then used in conventional hybridization assays, such as Southern or Northern hybridization assays, or polymerase chain reaction assays (PCR), to identify hybridizing DNA, cDNA, or RNA molecules. PCR assays may also be performed using unlabeled nucleic acid molecules. Such assays may be employed to identify AP-MDR vectors and transformants and in in vitro diagnosis to detect AP-MDR-like mRNA, cDNA, or genomic DNA from other organisms.

United States patent application Ser. No. 08/111680, the entire contents of which are hereby incorporated herein by reference, describes the use of combination therapy involving an antifungal agent possessing a proven spectrum of activity, with a fungal MDR inhibitor to treat fungal infections. This combination therapy approach enables an extension of the spectrum of antifungal activity for a given antifungal compound which previously had only demonstrated limited clinically relevant antifungal activity. Similarly, compounds with demonstrated antifungal activity can also be potentiated by a fungal MDR inhibitor such that the antifungal activity of these compounds is extended to previously resistant species. To identify compounds useful in such combination therapy the present invention provides an assay method for identifying compounds with MDR inhibition activity. Host cells that express AP-MDR provide an excellent means for the identification of compounds useful as inhibitors of fungal MDR activity. Generally, the assay utilizes a culture of a yeast cell transformed with a vector which provides expression of AP-MDR. The expression of the AP-MDR by the host cell enables the host cell to grow in the presence of an antifungal compound to which the yeast cell is sensitive to in the untransformed state. Thus, the transformed yeast cell culture is grown in the presence of i) an antifungal agent to which the untransformed yeast cell is sensitive, but to which the transformed host cell is resistant, and ii) a compound that is suspected of being an MDR inhibitor. The effect of the suspected MDR inhibitor is measured by testing for the ability of the antifungal compound to inhibit the growth of the transformed yeast cell. Such inhibition will occur if the suspected MDR inhibitor blocks the ability of the AP-MDR to prevent the antifungal compound from acting on the yeast cell. An illustrative example of such an assay is provided in Example 3.

In order to illustrate more fully the operation of this invention, the following examples are provided, but are not to be construed as a limitation on the scope of the invention.

EXAMPLE 1

Source of the MDR encoding DNA of *Aureobasidium pullulans*

Isolation of Plasmid pPSR3

A lyophil of *Escherichia coli* XL1-Blue/pPSR3 can be obtained from the Northern Regional Research Laboratories (NRRL), Peoria, Ill. 61604, under the accession number NRRL B-21202. Plasmid pPSR3 may be isolated from NRRL B-21202 using techniques that are well-known to those skilled in the art. See Sambrook et al., *Molecular Cloning: A Laboratory Manual* (1988), Cold Spring Harbor Laboratory Press, Cold Spring Harbor, N.Y. or Ausubel et al., *Current Protocols in Molecular Biology* (1989), John Wiley & Sons, New York, N.Y. and supplements.

EXAMPLE 2

Expression of the AP-MDR Protein

*Saccharomyces cerevisiae* INVSc1 cells (Invitrogen Corp., San Diego Calif. 92191) were transformed with the plasmid pPSR3 by the technique described by J. D. Beggs, 1988, *Nature* 275:104–109). The transformed yeast cells were grown in a broth medium containing YNB/CSM-Ura/raf (YNB/CSM-Ura [Yeast Nitrogen Base (Difco Laboratories, Detroit, Mich.) supplemented with CSM-URA (Bio 101, Inc.)] supplemented with 4% raffinose) at 28° C. in a shaker incubator until the culture was saturated. To induce expression of the AP-MDR, a portion of the culture was used to inoculate a flask containing YNB/CSM-Ura medium supplemented with 2% galactose (YNB/CSM-Ura/gal) rather than raffinose as the sole carbon source. The inoculated flsk was incubated at 28° C. for about 16 hours.

EXAMPLE 3

Antifungal Potentiator Assay

Approximately 1×10$^6$ cells of a *Saccharomyces cerevisiae* INVSc1/pPSR3 culture are delivered to each of several agar plates containing YNB/CSM-Ura/gal. The agar surface is allowed to dry in a biohazard hood. *Saccharomyces cerevisiae* INVSc1/pPSR3 cells express the AP-MDR activity.

An antifungal compound that the untransformed yeast cell is typically sensitive to, such as R106I (U.S. Pat. No. 5,057,493, which is hereby incorporated herein by reference), is dissolved in 100% ethanol at a concentration of either 1 or 7 mg/ml. Twenty µl of the 1 mg/ml solution is delivered to an antibiotic susceptibility test disc (Difco Laboratories, Detroit, Mich.). After addition of the antifungal solution the disc is allowed to air dry in a biohazard hood. When dry, the disc is placed on the surface of the petri plates containing the *Saccharomyces cerevisiae* INVSc1/pPSR3 cells.

Compounds to be tested for the ability to inhibit AP-MDR are dissolved in dimethylsulfoxide (DMSO). The amount of compound added to the DMSO depends on the solubility of the individual compound to be tested. Twenty µl of the suspensions containing a compound to be tested are delivered to an antibiotic susceptibility test disc (Difco Laboratories, Detroit, Mich.). The disc containing the test compounds is allowed to air dry in a biohazard hood. The disc is then placed on the surface of the dried petri plates containing the *Saccharomyces cerevisiae* INVSc1/pPSR3 cells approximately 2 cm from the antifungal-containing disc. Petri plates containing the two discs are incubated at 28° C. for about 16 hours.

Following this incubation period, the petri plates are examined for zones of growth inhibition around the discs. A zone of growth inhibition near the antifungal disc on the test plate indicates that the compound being tested for MDR inhibition activity blocks the activity of AP-MDR and allows the antifungal compound to inhibit the growth of the yeast host cell. Such compounds are said to possess MDR inhibition activity. Little or no zone of growth inhibition indicates that the test compound does not block MDR activity and, thus, the AP-MDR is allowed to act upon the antifungal compound to prevent its activity upon the host cell.

We claim:

1. An isolated nucleic acid molecule that encodes a multiple drug resistance protein of *Aureobasidium pullulans* (AP-MDR).

2. A nucleic acid molecule of claim 1 which is DNA.

3. The nucleic acid molecule of claim 2 that is SEQ. ID. No. 1.

4. A replicable vector comprising the nucleic acid of claim 1.

5. A replicable vector comprising the nucleic acid of claim 2.

6. A replicable vector comprising the nucleic acid of claim 3.

7. A host cell containing the vector of claim 4.

8. A host cell containing the vector of claim 5.

9. A host cell containing the vector of claim 6.

10. The host cell of claim 7 that is a yeast cell.

11. The host cell of claim 8 that is a yeast cell.

12. The host cell of claim 9 that is a yeast cell.

13. A method for producing *Aureobasidium pullulans* MDR in a host cell, said method comprising culturing the host cell of claim 10 under conditions suitable for expression of *Aureobasidium pullulans* MDR and purifying the AP-MDR protein.

14. A method for producing *Aureobasidium pullulans* MDR in a host cell, said method comprising culturing the host cell of claim 11 under conditions suitable for expression of *Aureobasidium pullulans* MDR and purifying the AP-MDR protein.

15. A method for producing *Aureobasidium pullulans* MDR in a host cell, said method comprising culturing the host cell of claim 12 under conditions suitable for expression of *Aureobasidium pullulans* MDR and purifying the AP-MDR protein.

* * * * *